US00PP26662P2

(12) United States Plant Patent
Shadow

(10) Patent No.: US PP26,662 P2
(45) Date of Patent: Apr. 26, 2016

(54) ALTHEA PLANT NAMED 'DS01BS'

(50) Latin Name: *Hibiscus syriacus*
Varietal Denomination: DS01BS

(71) Applicant: Don Odom Shadow, Winchester, TN (US)

(72) Inventor: Don Odom Shadow, Winchester, TN (US)

(73) Assignee: Greenleaf Nursery Company, Park Hill, OK (US)

( * ) Notice: Subject to any disclaimer, the term of this patent is extended or adjusted under 35 U.S.C. 154(b) by 32 days.

(21) Appl. No.: 13/986,868

(22) Filed: Jun. 13, 2013

(51) Int. Cl.
*A01H 5/02* (2006.01)

(52) U.S. Cl.
USPC ..... Plt./257

(58) Field of Classification Search
USPC ..... Plt./257, 226
CPC ..... A01H 5/02; A01H 5/00
See application file for complete search history.

(56) References Cited

U.S. PATENT DOCUMENTS

PP20,574 P2 * 12/2009 Woods ..... Plt./257

* cited by examiner

*Primary Examiner* — June Hwu
(74) *Attorney, Agent, or Firm* — C. A. Whealy

(57) ABSTRACT

A new and distinct cultivar of Althea plant named 'DS01BS', characterized by its upright, somewhat outwardly spreading and uniformly mounded plant habit; freely branching habit, dense and bushy plant form; medium green-colored leaves; early, uniform and freely flowering habit; long flowering period; large double-type ruffled violet blue-colored flowers that are not persistent; and good container and garden performance.

2 Drawing Sheets

Botanical designation: *Hibiscus syriacus*.
Cultivar denomination: 'DS01BS'.

BACKGROUND OF THE INVENTION

The present invention relates to a new and distinct Althea plant, botanically known as *Hibiscus syriacus*, also known as Rose of Sharon, and hereinafter referred to by the name 'DS01BS'.

The new Althea plant is a naturally-occurring whole plant mutation of an unnamed proprietary selection of *Hibiscus syriacus*, not patented. The new Althea plant was discovered and selected by the Inventor as a single flowering plant within a population of plants of the parent selection in a controlled nursery environment in Winchester, Tenn. in July, 2006.

Asexual reproduction of the new Althea plant by softwood cuttings in a controlled environment in Winchester, Tenn. since July, 2007 has shown that the unique features of this new Althea plant are stable and reproduced true to type in successive generations.

SUMMARY OF THE INVENTION

Plants of the new Althea have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DS01BS'. These characteristics in combination distinguish 'DS01BS' as a new and distinct Althea plant:

1. Upright, somewhat outwardly spreading and uniformly mounded plant habit.
2. Freely branching habit, dense and bushy plant form.
3. Medium green-colored leaves.
4. Early, uniform and freely flowering habit.
5. Long flowering period.
6. Large double-type ruffled violet blue-colored flowers that are not persistent.
7. Good container and garden performance.

Plants of the new Althea can be compared to plants of the parent selection. Plants of the new Althea differ from plants of the parent selection in the following characteristics:

1. Plants of the new Althea are more uniform, freely branching and denser than plants of the parent selection.
2. Flower color of plants of the new Althea is more uniform than flower color of plants of the parent selection.

Plants of the new Althea can be compared to plants of the *Hibiscus syriacus* 'Notwood3', disclosed in U.S. Plant Pat. No. 20,574. In side-by-side comparisons conducted in Winchester, Tenn., plants of the new Althea differed from plants of 'Notwood3' in the following characteristics:

1. Plants of the new Althea were smaller and more compact than plants of 'Notwood3'.
2. Plants of the new Althea and 'Notwood3' differed in flower color as plants of 'Notwood3' had blue-colored flowers.

BRIEF DESCRIPTION OF THE PHOTOGRAPHS

The accompanying colored photographs illustrate the overall appearance of the new Althea plant showing the colors as true as it is reasonably possible to obtain in colored reproductions of this type. Colors in the photographs may differ slightly from the color values cited in the detailed botanical description which accurately describe the colors of the new Althea plant.

The photograph on the first sheet is a side perspective view of a typical flowering plant of 'DS01BS' grown in a container.

The photograph on the second sheet is a close-up view of a typical open flower of 'DS01BS'.

DETAILED BOTANICAL DESCRIPTION

The aforementioned photographs and following observations, measurements and values describe plants grown during the summer in 15-cm containers in an outdoor nursery in Park Hill, Okla. and Fort Worth, Tex. under cultural practices typical of commercial Althea production. During the production of the plants, day temperatures ranged from 20° C. to 38° C., night temperatures ranged from 15° C. to 24° C. and light levels ranged from 3,000 to 4,000 foot-candles. Plants were pinched one time and were four years old when the photographs and the description were taken. In the description, color references are made to The Royal Horticultural Society Colour Chart, 2007 Edition, except where general terms of ordinary dictionary significance are used.

Botanical classification: *Hibiscus syriacus* 'DS01BS'.

Parentage: Naturally-occurring whole plant mutation an unnamed proprietary selection of *Hibiscus syriacus*, not patented.

Propagation:

*Type*.—By softwood cuttings in the summer and semi-hardwood cuttings in the winter; plants are typically propagated during the summer.

*Time to initiate roots, summer*.—About 14 to 18 days at soil temperatures about 24° C. to 27° C.

*Time to initiate roots, winter*.—About 20 to 25 days at soil temperatures about 24° C. to 27° C.

*Time to produce a rooted young plant, summer*.—About two to three months at soil temperatures about 24° C. to 27° C.

*Time to produce a rooted young plant, winter*.—About three to six months at soil temperatures about 16° C. to 21° C.

*Root description*.—Medium in thickness, fibrous; white in color.

*Rooting habit*.—Freely branching; dense.

Plant description:

*Plant and growth habit*.—Perennial shrub; upright, somewhat outwardly spreading and uniformly mounded plant habit; moderately vigorous to vigorous growth habit.

*Branching habit*.—Freely branching habit with lateral branches potentially develop at every node; pinching enhances lateral branch development; dense and bushy plant form.

*Plant height*.—About 67 cm.

*Plant diameter* (*area of spread*).—About 48 cm.

Lateral branch description:

*Length*.—About 29.5 cm.

*Diameter*.—About 4 mm.

*Internode length*.—About 3.6 cm.

*Aspect*.—Upright to outwardly spreading.

*Texture, immature*.—Smooth, glabrous.

*Texture, mature*.—Woody and somewhat rough.

*Luster, immature and mature*.—Matte, dull.

*Color, immature*.—Close to 195A.

*Color, mature*.—Close to 195A becoming closer to 199A and 199B with development.

Leaf description:

*Arrangement*.—Alternate, single.

*Length*.—About 10.25 cm.

*Width*.—About 7.5 cm.

*Shape*.—Overall outline, ovate; palmately lobed.

*Apex*.—Cuspidate.

*Base*.—Cuneate.

*Margin*.—Crenate; palmately lobed to varying depths, sinuses divergent.

*Texture, upper and lower surfaces*.—Smooth, glabrous.

*Luster, upper and lower surfaces*.—Matte, dull.

*Venation pattern*.—Pinnate; arcuate.

*Color*.—Developing leaves, upper surface: Close to 137C. Developing leaves, lower surface: Close to 144A. Fully expanded leaves, upper surface: Close to 137A to 137B; venation, close to 144A. Fully expanded leaves, lower surface: Darker than 144A; mid-vein, close to 145C and lateral veins, close to 144A.

*Petioles*.—Length: About 1.25 cm. Diameter: About 2 mm. Strength: Strong, flexible. Texture, upper and lower surfaces: Smooth, glabrous. Luster, upper and lower surfaces: Matte. Color, upper and lower surfaces: Close to 144A.

Flower description:

*Flower arrangement and flowering habit*.—Ruffled fully double- type flowers arranged at terminal leaf axils; uniform and freely flowering habit with about three to four flowers per terminal; flowers face mostly outwardly.

*Natural flowering season*.—Early flowering habit, plants of the new Althea begin flowering about seven weeks after pinching; long flowering period with plants flowering continuously from spring until the autumn in Oklahoma and Texas.

*Flower longevity*.—Flowers last about two to three days on the plant depending on temperature; flowers not persistent.

*Flower diameter*.—About 10 cm.

*Flower depth* (*height*).—About 3.5 cm to 4 cm.

*Flower buds*.—Length: About 1.75 cm. Diameter: About 1.2 cm. Shape: Ovoid. Texture: Rough, short pubescence. Luster: Matte, dull. Color: Close to 144A.

*Petals/petaloids*.—Arrangement: Corolla consists of multiple petals/petaloids in numerous whorls that are fused at base; petals/petaloids imbricate. Length (largest, outer): About 5.1 cm. Width (largest outer): About 3.6 cm. Shape: Roughly spatulate. Apex: Rounded. Base: Cuneate. Margin: Crenate; undulate, ruffled appearance. Texture, upper and lower surfaces: Smooth, glabrous; velvety; veins prominent on the lower surface. Luster, upper and lower surface: Matte. Color: When opening, upper surface: Close to 92B to 92D and 91C; towards the base, close to 59A. When opening, lower surface: Close to 92B to 92D and 91C; towards the base, close to 59B. Fully opened, upper surface: Towards the apex, close to 90A to 90C; mid-section, close to 92B to 92D and 91C; towards the base, close to 59A; venation, close to N87A and 59A. Fully opened, lower surface: Towards the apex, close to 90B to 90C; mid-section, close to 92B to 92D and 91C; towards the base, close to 59B; venation, close to N87A to N87B and 59B.

*Sepals*.—Appearance: Five sepals fused into a star-shaped calyx. Length: About 2 cm. Width: About 1 cm. Shape: Broadly lanceolate. Apex: Cuspidate. Base: Fused. Margin: Entire. Texture, upper surface: Smooth, glabrous. Texture, lower surface: Rough, short pubescence. Luster, upper surface: Somewhat glossy. Luster, lower surface: Matte, dull. Color, upper surface: Close to 144A to 144B. Color, lower surface: Close to 144A.

*Bracts*.—Appearance: About eight to ten fused at base. Length: About 9 mm. Width: About 2 mm. Shape: Acicular. Apex: Acute. Base: Fused. Margin: Entire. Texture, upper surface: Smooth, glabrous. Texture, lower surface: Rough, short pubescence. Luster, upper and lower surfaces: Matte, dull. Color, upper and lower surfaces: Close to 144A.

*Peduncles*.—Length: About 7 mm. Diameter: About 3.5 mm. Aspect: Upright to slightly outward. Strength: Strong, flexible. Texture: Rough, short pubescence. Color: Close to 144A.

*Reproductive organs*.—None observed, reproductive structures transformed into petaloids.

*Seeds and fruits*.—Seed and fruit production has not been observed on plants of the new Althea as flowers are sterile.

Garden performance: Plants of the new Althea have been observed to have good garden performance and to tolerate wind, rain and temperatures ranging from about −29° C. to about 43° C.

Pathogen & pest resistance: Plants of the new Althea have not been observed to be resistant to pathogens and pests common to Althea plants.

It is claimed:

1. A new and distinct Althea plant named 'DS01BS' as illustrated and described.

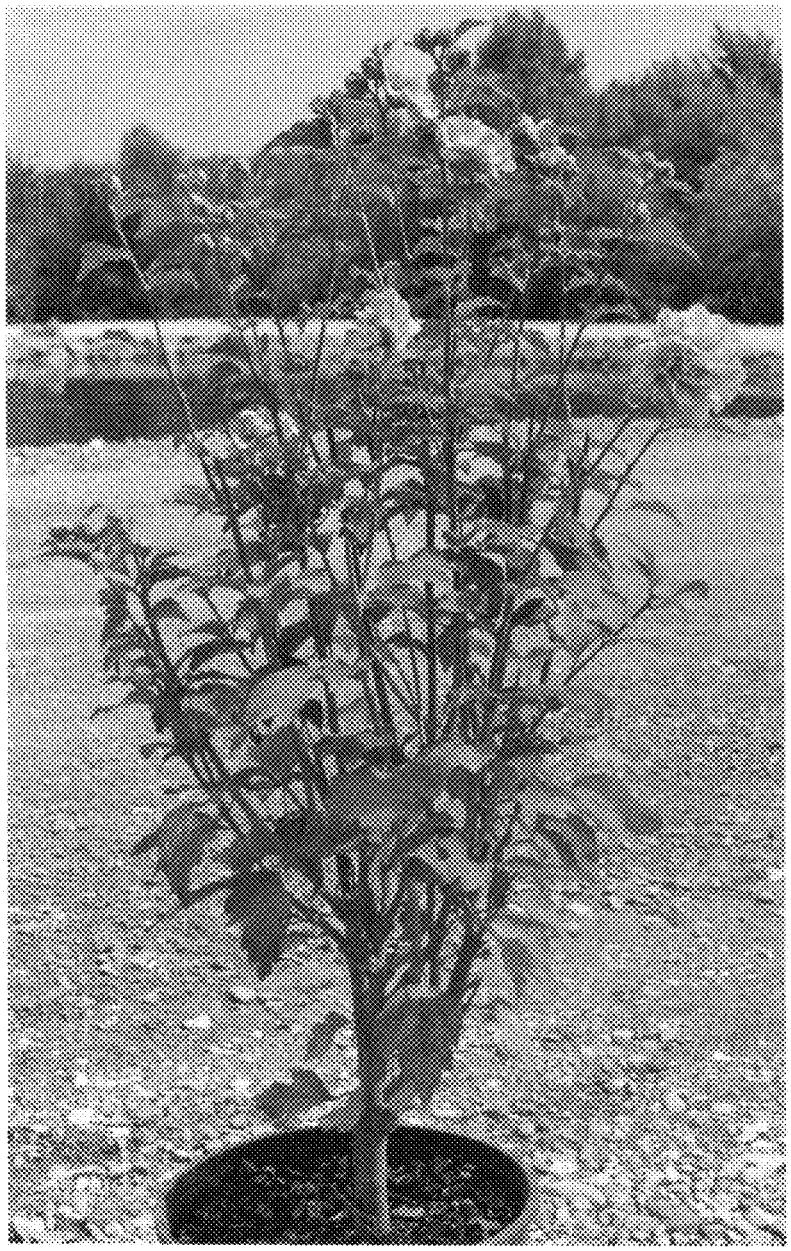

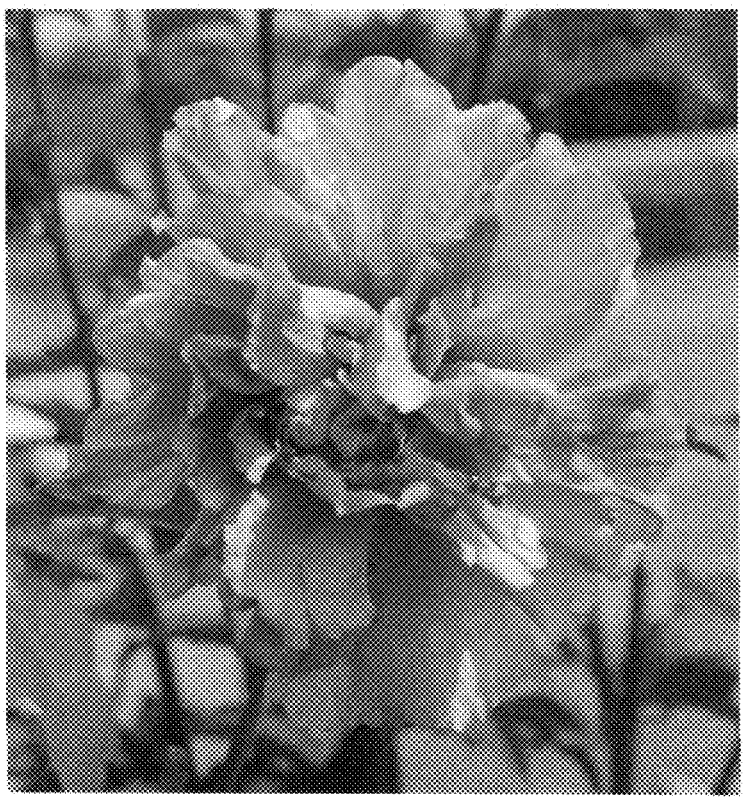

* * * * *